United States Patent [19]
Harris

[11] Patent Number: 5,837,469
[45] Date of Patent: Nov. 17, 1998

[54] **ASSAY FOR *CHLAMYDIA TRACHOMATIS* BY AMPLIFICATION AND DETECTION OF *CHLAMYDIA TRACHOMATIS* NUCLEIC ACID**

[75] Inventor: James M. Harris, Columbia, Md.

[73] Assignee: Becton Dickinson and Company, Franklin Lakes, N.J.

[21] Appl. No.: 963,933

[22] Filed: Nov. 4, 1997

[51] Int. Cl.⁶ .............................. C12Q 1/68; C07H 21/02
[52] U.S. Cl. ............................................... 435/6; 536/23.1
[58] Field of Search ................................. 435/6; 536/23.1

[56] References Cited
PUBLICATIONS

Fahr et al J. Bacteriol 177(15):4252–4260, 1995.

*Primary Examiner*—Eggerton A. Campbell
*Attorney, Agent, or Firm*—David W. Highet, Esq.

[57] ABSTRACT

A region of the *Chlamydia trachomatis* ltuB gene has been identified which is useful for performing amplification assays to determine specifically whether *C. trachomatis* is present in the sample being tested. Oligonucleotides useful for performing thermophilic Strand Displacement Assay (tSDA) reactions on this gene are disclosed. The disclosed oligonucleotides can be used in an assay which is specific for all strains of *C. trachomatis* and which does not show crossreactivity with the genomes of other microorganisms or with human DNA.

19 Claims, 1 Drawing Sheet

* Denotes the amplification primers chosen for further *1tuB* experimentation and studies.

5,837,469

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CCACTTCCAG AAATTGACA 19

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCAATATAGA GGGATAACG 19

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CGTACCAGAA TGGCTTTG 18

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CAAAGCCATT CTGGTAG 17

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

AAGAAGCAGT CGCAAGCT 18

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

AAAGTGCATC TCTGTAGC                                                                                    18

( 2 ) INFORMATION FOR SEQ ID NO:7:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

ACCGCATCGA ATGCATGTCT CGGGTTACGT ACCAGAATGG                                                             40

( 2 ) INFORMATION FOR SEQ ID NO:8:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

ACCGCATCGA ATGCATGTCT CGGGTTACGT ACCAGAATG                                                              39

( 2 ) INFORMATION FOR SEQ ID NO:9:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CGATTCCGCT CCAGACTTCT CGGGTTCACA GAATATCGCC                                                             40

( 2 ) INFORMATION FOR SEQ ID NO:10:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CGATTCCGCT CCAGACTTCT CGGGTTCACA GAATATCGC                                                              39

( 2 ) INFORMATION FOR SEQ ID NO:11:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

AAATTCTGAC CAAGTT                                                                                      16

( 2 ) INFORMATION FOR SEQ ID NO:12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
TTTGATCTTT CTCCC                                                        15
```

( 2 ) INFORMATION FOR SEQ ID NO:13:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:13:

```
GGCTTTGTGG AGACA                                                        15
```

( 2 ) INFORMATION FOR SEQ ID NO:14:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:14:

```
GACTTTCATA ATTTTGG                                                      17
```

ASSAY FOR *CHLAMYDIA TRACHOMATIS* BY AMPLIFICATION AND DETECTION OF *CHLAMYDIA TRACHOMATIS* NUCLEIC ACID

FIELD OF THE INVENTION

The present invention relates to methods for determining the presence or absence of *Chlamydia trachomatis* in patients. The method involves using nucleic acid primers to amplify specifically *Chlamydia trachomatis* ltuB nucleic acid, preferably using one of the techniques of Strand Displacement Amplification (SDA), thermophilic Strand Displacement Amplification (tSDA) or fluorescent real time tSDA.

BACKGROUND OF THE INVENTION

*Chlamydia trachomatis* is the causative agent of trachoma (which is the greatest single cause of blindness), inclusion conjunctivitis, infant pneumonitis, urethritis and lymphogranuloma venereum. Diagnosis and detection of this organism is often on the basis of the pathologic or clinical findings and may be confirmed by isolation and staining techniques.

*C. trachomatis* includes a gene called ltuB. This gene was discovered in 1995 by Hatch et al. (Fahr et al., *J. Bacteriol.* 177:4252–4260 (1995)). The ltuB gene was found to be responsible for the production of two specific messenger RNAs (T1 and T2). These transcripts were determined to be synthesized in large quantities during a stage specific switch that involves the bacteria transforming itself from a reticulate body (RB) to an elementary body (EB). Reticulate bodies are the noninfectious form of the bacteria, with EB being the opposite. The ltuB gene encodes both mRNA transcripts, with T2 believed to be a post-transcriptional modification of the larger T1 mRNA.

The following terms are defined herein as follows:

An amplification primer is a primer for amplification of a target sequence by extension of the primer after hybridization to the target sequence. Amplification primers are typically about 10–75 nucleotides in length, preferably about 15–50 nucleotides in length. The total length of an amplification primer for SDA is typically about 25–50 nucleotides. The 3' end of an SDA amplification primer (the target binding sequence) hybridizes at the 5' end of the target sequence. The target binding sequence is about 10–25 nucleotides in length and confers hybridization specificity on the amplification primer. The SDA amplification primer further comprises a recognition site for a restriction endonuclease 5' to the target binding sequence. The recognition site is for a restriction endonuclease which will nick one strand of a DNA duplex when the recognition site is hemimodified, as described by G. Walker, et al. (1992. *PNAS* 89:392–396 and 1992 *Nucl. Acids Res.* 20:1691–1696). The nucleotides 5' to the restriction endonuclease recognition site (the "tail") function as a polymerase repriming site when the remainder of the amplification primer is nicked and displaced during SDA. The repriming function of the tail nucleotides sustains the SDA reaction and allows synthesis of multiple amplicons from a single target molecule. The tail is typically about 10–25 nucleotides in length. Its length and sequence are generally not critical and can be routinely selected and modified to obtain the desired $T_m$ for hybridization. As the target binding sequence is the portion of a primer which determines its target-specificity, for amplification methods which do not require specialized sequences at the ends of the target the amplification primer generally consists essentially of only the target binding sequence. For amplification methods which require specialized sequences appended to the target other than the nickable restriction endonuclease recognition site and the tail of SDA (e.g., an RNA polymerase promoter for 3SR, NASBA or transcription based amplification), the required specialized sequence may be linked to the target binding sequence using routine methods for preparation of oligonucleotides without altering the hybridization specificity of the primer.

A bumper primer or external primer is a primer used to displace primer extension products in isothermal amplification reactions. The bumper primer anneals to a target sequence upstream of the amplification primer such that extension of the bumper primer displaces the downstream amplification primer and its extension product.

The terms target or target sequence refer to nucleic acid sequences to be amplified. These include the original nucleic acid sequence to be amplified, the complementary second strand of the original nucleic acid sequence to be amplified and either strand of a copy of the original sequence which is produced by the amplification reaction. These copies serve as amplifiable targets by virtue of the fact that they contain copies of the sequence to which the amplification primers hybridize.

Copies of the target sequence which are generated during the amplification reaction are referred to as amplification products, amplimers or amplicons.

The term extension product refers to the copy of a target sequence produced by hybridization of a primer and extension of the primer by polymerase using the target sequence as a template.

The term species-specific refers to detection, amplification or oligonucleotide hybridization in a species of organism or a group of related species without substantial detection, amplification or oligonucleotide hybridization in other species of the same genus or species of a different genus.

The term assay probe refers to any oligonucleotide used to facilitate detection or identification of a nucleic acid. For example, in the present invention, assay probes are used for detection or identification of *C. trachomatis* ltuB nucleic acids. Detector probes, detector primers, capture probes and signal primers as described below are examples of assay probes.

SUMMARY OF THE INVENTION

The present invention provides oligonucleotides useful as amplification primers and assay probes for specific detection and identification of *Chlamydia trachomatis*. The specific oligonucleotides are used to amplify the *C. trachomatis* ltuB nucleic acid with little or no detectable amplification of either human DNA or DNA of other microorganisms.

The oligonucleotides of the invention may be used after culture as a means for confirming the identity of the cultured organism. Alternatively, the oligonucleotides may be used prior to culture or in place of culture for detection and identification of *C. trachomatis* using known amplification methods. In either case, the oligonucleotides and assay methods of the present invention provide a means for discriminating between *C. trachomatis* and other microorganisms, allowing the practitioner to identify rapidly this microorganism without resorting to the more traditional procedures customarily relied upon. Such rapid identification of the specific etiological agent involved in an infection provides information which can be used to determine appropriate therapy within a short period of time.

BRIEF DESCRIPTION OF THE DRAWINGS

The various objects, advantages and novel features of the present invention will be readily understood from the fol

DETAILED DESCRIPTION OF THE INVENTION

Figure 1:
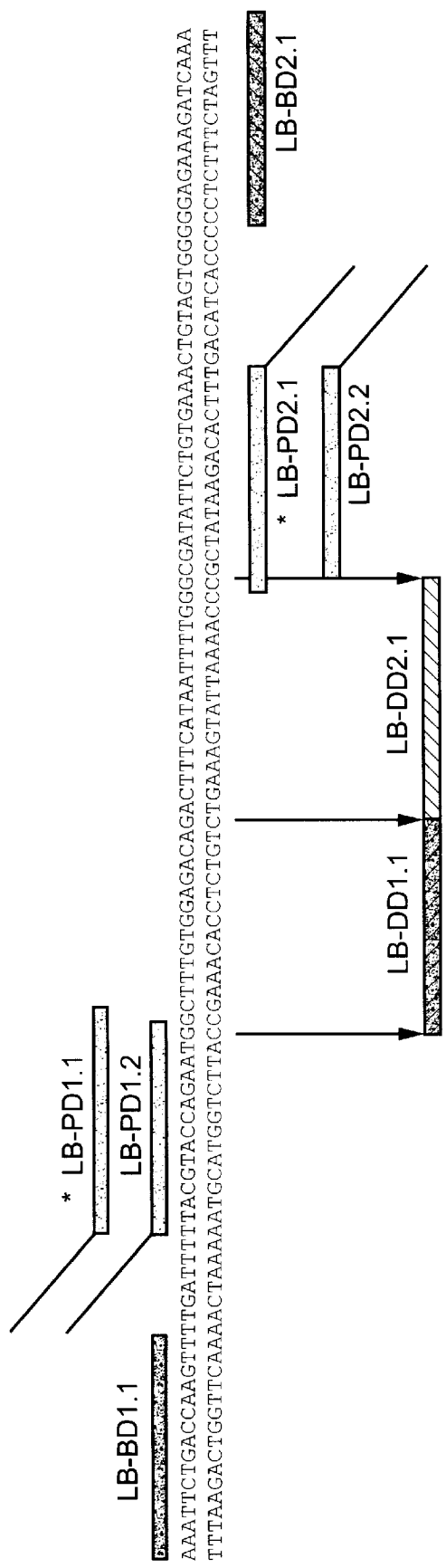
- FIG. 1 shows a partial ltuB sequence and indicates the positions of primers, bumpers and detectors utilized for tSDA.

The present invention provides oligonucleotides, amplification primers and assay probes which exhibit *Chlamydia trachomatis*-specificity in nucleic acid amplification reactions. Also provided are methods for detecting and identifying *C. trachomatis* ltuB nucleic acids using the oligonucleotides of the invention. The preferred methods are to use SDA, tSDA or homogeneous real time fluorescent tSDA. These methods are taught by U.S. Pat. No. 5,547,861, U.S. Pat. No. 5,648,211, U.S. Ser. No. 08/865,675, filed May 30, 1997 and U.S. Ser. No. 08/855,085, filed May 13, 1997, the disclosures of which are specifically incorporated herein by reference.

Because of its role during the switch between life-cycles it was hypothesized by the inventors of the present invention that the ltuB gene might be species-specific. Database searches were performed but proved to be negative for the protein that is hypothetically encoded by two open reading frames within the ltuB gene. The gene was studied to develop nucleic acid primers which would specifically amplify this gene in all *Chlamydia trachomatis* serovars without showing crossreactivity with human DNA or other microorganism DNA.

Primers were designed based on the sequence of *C. trachomatis* ltuB gene which was available from GenBank. Using these primers, the sequence of the ltuB gene in several *C. trachomatis* serovars was determined, and the identification of a homologous gene in other species was attempted. Various combinations of primers were tested for specificity and sensitivity in tSDA reactions.

As nucleic acids do not require complete complementarity in order to hybridize, it is to be understood that the probe and primer sequences herein disclosed may be modified to some extent without loss of utility as *C. trachomatis*-specific probes and primers. As is known in the art, hybridization of complementary and partially complementary nucleic acid sequences may be obtained by adjustment of the hybridization conditions to increase or decrease stringency (i.e., adjustment of hybridization temperature or salt content of the buffer). Such minor modifications of the disclosed sequences and any necessary adjustments of hybridization conditions to maintain *C. trachomatis*-specificity require only routine experimentation and are within the ordinary skill in the art.

The amplification products generated using the primers of the present invention may be detected by a characteristic size, for example on polyacrylamide or agarose gels stained with ethidium bromide. Alternatively, amplified *C. trachomatis* ltuB gene target sequences may be detected by means of an assay probe, which is an oligonucleotide tagged with a detectable label. In one embodiment, at least one tagged assay probe may be used for detection of amplified target sequences by hybridization (a detector probe), by hybridization and extension as described by Walker, et al., *Nucl. Acids Res.*, supra (a detector primer) or by hybridization, extension and conversion to double stranded form as described in EP 0 678 582 (a signal primer). Preferably, the assay probe is selected to hybridize to a sequence in the target which is between the amplification primers, i.e., it should be an internal assay probe. Alternatively, an amplification primer or the target binding sequence thereof may be used as the assay probe.

The detectable label of the assay probe is a moiety which can be detected either directly or indirectly as an indication of the presence of the target nucleic acid. For direct detection of the label, assay probes may be tagged with a radioisotope and detected by autoradiography or tagged with a fluorescent moiety and detected by fluorescence as is known in the art. Alternatively, the assay probes may be indirectly detected by tagging with a label which requires additional reagents to render it detectable. Indirectly detectable labels include, for example, chemiluminescent agents, enzymes which produce visible reaction products and ligands (e.g., haptens, antibodies or antigens) which may be detected by binding to labeled specific binding partners (e.g., antibodies or antigens/haptens). Ligands are also useful immobilizing the ligand-labeled oligonucleotide (the capture probe) on a solid phase to facilitate its detection. Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

Examples of specific detection methods which may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of the two amplification primers), the complex is captured on a streptavidin-coated microtiter plate by means of the capture probe, and the chemiluminescent signal is developed and read in a luminometer. As another alternative for detection of amplification products, a signal primer as described in EP 0 678 582 may be included in the SDA reaction. In this embodiment, labeled secondary amplification products are generated during SDA in a target amplification-dependent manner and may be detected as an indication of target amplification by means of the associated label.

For commercial convenience, amplification primers for specific detection and identification of *C. trachomatis* ltuB nucleic acids may be packaged in the form of a kit. Typically, such a kit contains at least one pair of amplification primers according to the present invention. Reagents for performing a nucleic acid amplification reaction may also be included with the *C. trachomatis* ltuB-specific amplification primers, for example, buffers, additional primers, nucleotide triphosphates, enzymes, etc. The components of the kit are packaged together in a common container, optionally including instructions for performing a specific embodiment of the inventive methods. Other optional components may also be included in the kit, e.g., an oligonucleotide tagged with a label suitable for use as an assay probe, and/or reagents or means for detecting the label.

The target binding sequences of the amplification primers and detectors can confer species hybridization specificity on the oligonucleotides and therefore provide species-specificity to the amplification reaction. Other sequences, as required for performance of a selected amplification reaction, may optionally be added to the target binding sequences disclosed herein without altering the species-specificity of the oligonucleotide. By way of example, the *C. trachomatis* ltuB-specific amplification primers of the invention may contain a recognition site for the restriction endonuclease BsoBI which is nicked during the SDA reaction. It will be apparent to one skilled in the art that other nickable restriction endonuclease recognition sites may be substituted for the BsoBI recognition site, including but not limited to those recognition sites disclosed in EP 0 684 315. Preferably, the recognition site is for a thermophilic restriction endonuclease so that the amplification reaction may be performed under the conditions of thermophilic SDA (tSDA). Similarly, the tail sequence of the amplification primer (5' to the restriction endonuclease recognition site) is generally not critical, although the restriction site used for SDA and sequences which will hybridize either to their own target binding sequence or to the other primers should be avoided. Therefore, amplification primers of the present invention which are useful in SDA consist of 3' target binding sequences, a nickable restriction endonuclease recognition site 5' to the target binding sequence and a tail sequence about 10–25 nucleotides in length 5' to the restriction endonuclease recognition site. The nickable restriction endonuclease recognition site and the tail sequence are sequences required for the SDA reaction. For other amplification reactions, the amplification primers of the present invention may consist of the disclosed target binding sequences only (e.g., for PCR) or the target binding sequence and additional sequences required for the selected amplification reaction (e.g., sequences required for SDA as described above or a promoter recognized by RNA polymerase for 3SR).

In SDA, the bumper primers are not essential for species-specificity, as they function to displace the downstream, species-specific amplification primers. It is only required that the bumper primers hybridize to the target upstream from the amplification primers so that when they are extended they will displace the amplification primer and its extension product. The particular sequence of the bumper primer is therefore generally not critical, and may be derived from any upstream target sequence which is sufficiently close to the binding site of the amplification primer to allow displacement of the amplification primer extension product upon extension of the bumper primer. Occasional mismatches with the target in the bumper primer sequence or some cross-hybridization with non-target sequences do not generally negatively affect amplification efficiency as long as the bumper primer remains capable of hybridizing to the specific target sequence. However, the bumper primers described herein are species-specific for *C. trachomatis* and may therefore also be used as target binding sequences in amplification primers, if desired.

Amplification reactions employing the primers of the invention may incorporate thymine as taught by Walker, et al., supra, or they may wholly or partially substitute 2'-deoxyuridine 5'-triphosphate for TTP in the reaction to reduce cross-contamination of subsequent amplification reactions, e.g., as taught in EP 0 624 643. dU (uridine) is incorporated into amplification products and can be excised by treatment with uracil DNA glycosylase (UDG). These abasic sites render the amplification product unamplifiable in subsequent amplification reactions. UDG may be inactivated by uracil DNA glycosylase inhibitor (Ugi) prior to performing the subsequent amplification to prevent excision of dU in newly-formed amplification products.

Strand Displacement Amplification (SDA) is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occurs concurrently in the reaction mix. This is in contrast to the PCR, in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature. Production of each new copy of the target sequence consists of five steps: 1) binding of amplification primers to an original target sequence or a displaced single-stranded extension product previously polymerized, 2) extension of the primers by a 5'-3' exonuclease deficient polymerase incorporating an α-thio deoxynucleoside triphosphate (α-thio dNTP), 3) nicking of a hemimodified double stranded restriction site, 4) dissociation of the restriction enzyme from the nick site, and 5) extension from the 3' end of the nick by the 5'-3' exonuclease deficient polymerase with displacement of the downstream newly synthesized strand. Nicking, polymerization and displacement occur concurrently and continuously at a constant temperature because extension from the nick regenerates another nickable restriction site. When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an α-thio dNTP is incorporated are HincII, HindII, AvaI, NciI and Fnu4HI. All of these restriction endonucleases and others which display the required nicking activity are suitable for use in conventional SDA. However, they are relatively thermolabile and tend to lose activity above about 40° C.

Targets for amplification by SDA may be prepared by fragmenting larger nucleic acids by restriction with an endonuclease which does not cut the target sequence. However, it is generally preferred that target nucleic acids having the selected restriction endonuclease recognition/cleavage sites for nicking in the SDA reaction be generated as described by Walker, et al. (1992, *Nuc. Acids Res.*, supra) and in U.S. Pat. No. 5,270,184 (hereby incorporated by reference). Briefly, if the target sequence is double stranded, four primers are hybridized to it. Two of the primers ($S_1$ and $S_2$) are SDA amplification primers and two ($B_1$ and $B_2$) are external or bumper primers. $S_1$ and $S_2$ bind to opposite strands of double stranded nucleic acids flanking the target sequence. $B_1$ and $B_2$ bind to the target sequence 5' (i.e., upstream) of $S_1$ and S2, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATPαS"). The extension products of $S_1$ and $S_2$ are thereby displaced form the original target sequence template by extension of $B_1$ and $B_2$. The displaced, single stranded extension products of the amplification primers serve as targets for binding of the opposite amplification and bumper primer (e.g., the extension product of $S_1$ binds $S_2$ and $B_2$). The next cycle of extension and displacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA cycle and are amplified.

To prevent cross-contamination of one SDA reaction by the amplification products of another, dUTP may be incorporated into SDA-amplified DNA in place of dTTP without inhibition of the amplification reaction. The uracil-modified nucleic acids may then be specifically recognized and inactivated by treatment with UDG. Therefore, if dUTP is incorporated into SDA-amplified DNA in a prior reaction, any subsequent SDA reactions can be treated with UDG prior to amplification of double stranded targets, and any dU containing DNA from previously amplified reactions will be rendered unamplifiable. The target DNA to be amplified in the subsequent reaction does not contain dU and will not be affected by the UDG treatment. UDG may then be inhibited by treatment with Ugi prior to amplification of the target. Alternatively, UDG may be heat-inactivated. In thermophilic SDA, the higher temperature of the reaction itself ($\geq 50°$ C.) can be used to concurrently inactivate UDG and amplify the target.

SDA requires a polymerase which lacks 5'-3' exonuclease activity, initiates polymerization at a single stranded nick in double stranded nucleic acids, and displaces the strand downstream of the nick while generating a new complementary strand using the unnicked strand as a template. The polymerase must extend by adding nucleotides to a free 3'-OH. To optimize the SDA reaction, it is also desirable that the polymerase be highly processive to maximize the length of target sequence which can be amplified. Highly processive polymerases are capable of polymerizing new strands of significant length before dissociating and terminating synthesis of the extension product. Displacement activity is essential to the amplification reaction, as it makes the target available for synthesis of additional copies and generates the single stranded extension product to which a second amplification primer may hybridize in exponential amplification reactions.

Thermophilic SDA is performed essentially as the conventional SDA described by Walker, et al. (1992, *PNAS* and *Nuc. Acids Res.*, supra), with substitution of the desired thermostable polymerase and thermostable restriction endonuclease. Of course, the temperature of the reaction will be adjusted to the higher temperature suitable for the substituted enzymes and the HincII restriction endonuclease recognition/cleavage site will be replaced by the appropriate restriction endonuclease recognition/cleavage site for the selected thermostable endonuclease. Also in contrast to Walker, et al., the practitioner may include the enzymes in the reaction mixture prior to the initial denaturation step if they are sufficiently stable at the denaturation temperature. Preferred restriction endonucleases for use in thermophilic SDA are BsrI, BstNI, BsmAI, BSlI and BsoBI (New England BioLabs), and BstOI (Promega). The preferred thermophilic polymerases are Bca (Panvera) and Bst (New England Biolabs).

Homogeneous real time fluorescent tSDA is a modification of tSDA. It employs detector oligonucleotides to produce reduced fluorescence quenching in a target-dependent manner. The detector oligonucleotides contain a donor/acceptor dye pair linked such that fluorescence quenching occurs in the absence of target. Unfolding or linearization of an intramolecularly base-paired secondary structure in the detector oligonucleotide in the presence of the target increases the distance between the dyes and reduces fluorescence quenching. Unfolding of the base-paired secondary structure typically involves intermolecular base-pairing between the sequence of the secondary structure and a complementary strand such that the secondary structure is at least partially disrupted. It may be fully linearized in the presence of a complementary strand of sufficient length. In a preferred embodiment, a restriction endonuclease recognition site (RERS) is present between the two dyes such that intermolecular base-pairing between the secondary structure and a complementary strand also renders the RERS double-stranded and cleavable or nickable by a restriction endonuclease. Cleavage or nicking by the restriction endonuclease separates the donor and acceptor dyes onto separate nucleic acid fragments, further contributing to decreased quenching. In either embodiment, an associated change in a fluorescence parameter (e.g., an increase in donor fluorescence intensity, a decrease in acceptor fluorescence intensity or a ratio of fluorescence before and after unfolding) is monitored as an indication of the presence of the target sequence. Monitoring a change in donor fluorescence intensity is preferred, as this change is typically larger than the change in acceptor fluorescence intensity. Other fluorescence parameters such as a change in fluorescence lifetime may also be monitored.

A detector oligonucleotide for homogeneous real time fluorescent tSDA is an oligonucleotide which comprises a single-stranded 5' or 3' section which hybridizes to the target sequence (the target binding sequence) and an intramolecularly base-paired secondary structure adjacent to the target binding sequence. The detector oligonucleotides of the invention further comprise a donor/acceptor dye pair linked to the detector oligonucleotide such that donor fluorescence is quenched when the secondary structure is intramolecularly base-paired and unfolding or linearization of the secondary structure results in a decrease in fluorescence quenching. Cleavage of an oligonucleotide refers to breaking the phosphodiester bonds of both strands of a DNA duplex or breaking the phosphodiester bond of single-stranded DNA. This is in contrast to nicking, which refers to breaking the phosphodiester bond of only one of the two strands in a DNA duplex.

The detector oligonucleotides of the invention for homogeneous real time fluorescent tSDA comprise a sequence which forms an intramolecularly base-paired secondary structure under the selected reaction conditions for primer extension or hybridization. The secondary structure is positioned adjacent to the target binding sequence of the detector oligonucleotide so that at least a portion of the target binding sequence forms a single-stranded 3' or 5' tail. As used herein, the term "adjacent to the target binding sequence" means that all or part of the target binding sequence is left single-stranded in a 5' or 3' tail which is available for hybridization to the target. That is, the secondary structure does not comprise the entire target binding sequence. A portion of the target binding sequence may be involved in the intramolecular base-pairing in the secondary structure, it may include all or part of a first sequence involved in intramolecular base-pairing in the secondary structure, it may include all or part of a first sequence involved in intramolecular base-pairing in the secondary structure but preferably does not extend into its complementary sequence. For example, if the secondary structure is a stem-loop structure (e.g., a "hairpin") and the target binding sequence of the detector oligonucleotide is present as a single-stranded 3' tail, the target binding sequence may also extend through all or part of the first arm of the stem and, optionally, through all or part of the loop. However, the target binding sequence preferably does not extend into the second arm of the sequence involved in stem intramolecular base-pairing. That is, it is desirable to avoid having both sequences involved in intramolecular base-pairing in a secondary structure capable of hybridizing to the target. Mismatches in the intramolecularly base-paired portion of the detector oligonucleotide secondary structure may reduce the magnitude of the change in fluorescence in the presence of target but are acceptable if assay sensitivity is not a concern. Mismatches in the target binding sequence of the single-stranded tail are also acceptable but may similarly reduce assay sensitivity and/or specificity. However, it is a feature of the present invention that perfect base-pairing in both the secondary structure and the target binding sequence do not compromise the reaction. Perfect matches in the sequences involved in hybridization improve assay specificity without negative effects on reaction kinetics.

When added to the amplification reaction, the detector oligonucleotides of the invention are converted to double-stranded form by hybridization and extension of an amplification primer as described above. Strand displacement by the polymerase also unfolds or linearizes the secondary structure and converts it to double-stranded form by synthesis of a complementary strand. The RERS, if present, also becomes double-stranded and cleavable or nickable by the restriction endonuclease. As the secondary structure is unfolded or linearized by the strand displacing activity of the polymerase, the distance between the donor and acceptor dye is increased, thereby reducing quenching of donor fluorescence. The associated change in fluorescence of either the donor or acceptor dye may be monitored or detected as an indication of amplification of the target sequence. Cleavage or nicking of the RERS generally further increases the magnitude of the change in fluorescence by producing two separate fragments of the double-stranded secondary amplification product, each having one of the two dyes linked to it. These fragments are free to diffuse in the reaction solution, further increasing the distance between the dyes of the donor/acceptor pair. An increase in donor fluorescence intensity or a decrease in acceptor fluorescence intensity may be detected and/or monitored as an indication that target amplification is occurring or has occurred, but other fluorescence parameters which are affected by the proximity of the donor/acceptor dye pair may also be monitored. A change in fluorescence intensity of the donor or acceptor may also be detected as a change in a ratio of donor and/or acceptor fluorescence intensities. For example, a change in fluorescence intensity may be detected as a) an increase in the ratio of donor fluorophore fluorescence after linearizing or unfolding the secondary structure and donor fluorophore fluorescence in the detector oligonucleotide prior to linearizing or unfolding, or b) as a decrease in the ratio of acceptor dye fluorescence after linearizing or unfolding and acceptor dye fluorescence in the detector oligonucleotide prior to linearizing or unfolding.

It will be apparent that, in addition to SDA, the detector oligonucleotides of the invention may be adapted for use as signal primers in other primer extension amplification methods (e.g., PCR, 3SR, TMA or NASBA). For example, the methods may be adapted for use in PCR by using PCR amplification primers and a strand displacing DNA polymerase which lacks 5'→3' exonuclease activity (e.g., Sequencing Grade Taq from Promega or exo⁻ Vent or exo⁻ Deep Vent from New England BioLabs) in the PCR. The detector oligonucleotide signal primers hybridize to the target downstream from the PCR amplification primers, are displaced and are rendered double-stranded essentially as described for SDA. In PCR any RERS may optionally be selected for use in the detector oligonucleotide, as there are typically no modified deoxynucleoside triphosphates present which might induce nicking rather than cleavage of the RERS. As thermocycling is a feature of amplification by PCR, the restriction endonuclease is preferably added at low temperature after the final cycle of primer annealing and extension for end-point detection of amplification. However, a thermophilic restriction endonuclease which remains active through the high temperature phases of the PCR reaction could be present during amplification to provide a real-time assay. As in SDA systems, linearization of the secondary structure and separation of the dye pair reduces fluorescence quenching, with a change in a fluorescence parameter such as intensity serving as an indication of target amplification.

The change in fluorescence resulting from unfolding or linearizing of the detector oligonucleotides may be detected at a selected endpoint in the reaction. However, because linearized secondary structures are produced concurrently with hybridization or primer extension, the change in fluorescence may also be monitored as the reaction is occurring, i.e., in "real-time". This homogeneous, real-time assay format can be used to provide semiquantitative or quantitative information about the initial amount of target present. For example, the rate at which fluorescence intensity changes during the unfolding or linearizing reaction (either as part of target amplification or in non-amplification detection methods) is an indication of initial target levels. As a result, when more initial copies of the target sequence are present, donor fluorescence more rapidly reaches a selected threshold value (i.e., shorter time to positivity). The decrease in acceptor fluorescence similarly exhibits a shorter time to positivity, detected as the time required to reach a selected minimum value. In addition, the rate of change in fluorescence parameters during the course of the reaction is more rapid in samples containing higher initial amounts of target than in samples containing lower initial amounts of target (i.e., increased slope of the fluorescence curve). These or other measurements as is known in the art may be made as an indication of the presence of target or as an indication of target amplification. The initial amount of target is typically determined by comparison of the experimental results to results for known amounts of target.

Assays for the presence of a selected target sequence according to the methods of the invention may be performed in solution or on a solid phase. Real-time or endpoint homogeneous assays in which the detector oligonucleotide functions as a primer are typically performed in solution. Hybridization assays using the detector oligonucleotides of the invention may also be performed in solution (e.g., as homogeneous real-time assays) but are also particularly well-suited to solid phase assays for real-time or endpoint detection of target. In a solid phase assay, detector oligonucleotides may be immobilized on the solid phase (e.g., beads, membranes or the reaction vessel) via internal or terminal labels using methods known in the art. For example, a biotin-labeled detector oligonucleotide may be immobilized on an avidin-modified solid phase where it will produce a change in fluorescence when exposed to the target under appropriate hybridization conditions. Capture of the target in this manner facilitates separation of the target from the sample and allows removal of substances in the sample which may interfere with detection of the signal or other aspects of the assay.

The following Examples illustrate specific embodiments of the invention described herein. As would be apparent to skilled artisans, various changes and modifications are possible, and are contemplated within the scope of the invention described.

EXAMPLE 1

Initial Assay of the Specificity and Crossreactivity of Primers Based on ltuB

The original ltuB sequence was discovered in the GenBank/EMBL databases using the Geneworks™ software program. The deposited sequence (CHTLTUB) was obtained from a *C. trachomatis* LGV II serovar. A series of primers (for example, ltuB-1 and ltuB-2) were designed that flanked and are positioned within the section of the genome coding for the ltuB gene. Additional primers were designed that are positioned within the open reading frames of the ltuB gene. These primers were used in an experiment to amplify the ltuB region from the genomes of various *C. trachomatis* serovars and the crossreactants *C. psittaci* and *C. pneumoniae*. The primers used were:

| | |
|---|---|
| ltuB-1 | 5'-CCACTTCCAGAAATTGACA-3' (SEQ ID NO:1) |
| ltuB-2 | 5'-GCAATATAGAGGGATAACG-3' (SEQ ID NO:2) |
| ltuB-3 | 5'-CGTACCAGAATGGCTTTG-3' (SEQ ID NO:3) |
| ltuB-4 | 5'-CAAAGCCATTCTGGTAG-3' (SEQ ID NO:4) |
| ltuB-5 | 5'-AAGAAGCAGTCGCAAGCT-3' (SEQ ID NO:5) |
| ltuB-6 | 5'-AAAGTGCATCTCTGTAGC-3' (SEQ ID NO:6) |

A partial ltuB (CHTLTUB) sequence and the locations of the primers are shown in FIG. 1. Amplification using the above primers was performed, and the results are shown in Table 1. All of the tested strains of *C. trachomatis* yielded positive results while the *C. psittaci* and *C. pneumoniae* gave negative results. These initial results indicated that the ltuB gene could be species specific for *C. trachomatis*.

TABLE 1

| Organism | Strain | ltuB |
|---|---|---|
| Chlamydia trachomatis | A | + |
| Chlamydia trachomatis | B | + |
| Chlamydia trachomatis | Ba | + |
| Chlamydia trachomatis | C | + |
| Chlamydia trachomatis | D | + |
| Chlamydia trachomatis | E | + |
| Chlamydia trachomatis | F | + |
| Chlamydia trachomatis | G | + |
| Chlamydia trachomatis | H | + |
| Chlamydia trachomatis | I | + |
| Chlamydia trachomatis | J | + |
| Chlamydia trachomatis | K | + |
| Chlamydia trachomatis | LGV II | + |
| Chlamydia trachomatis | LGV III | + |
| Chlamydia psittaci | | − |
| Chlamydia pneumoniae | | − |

EXAMPLE 2

Sequencing of ltuB in Several Serovars of *C. trachomatis* and Design of an ltuB tSDA System The amplified products obtained in Example 1 were purified, further amplified, and then sequenced. A combination of flanking and internal primers (as shown in FIG. 1) were used to obtain a complete sequence of the ltuB gene from six strains of *C. trachomatis*. These included serovars A, C, D, E, H and L3.

A sequence alignment of these sequences was examined for potential regions that would be beneficial to tSDA and a section was selected for a tSDA primer set. The Oligo™ software program was used in determining whether a particular primer set should be used. This software program allows for the determination of interactions between all of the primers constituting the particular tSDA system. The names and sequences of all of the tSDA primers which were selected for testing were:

Upstream Primers

LB-PD1.1  5'-ACCGCATCGAATGCATGTCTCGGGTTACGTACCAGAATGG-3' (SEQ ID NO:7)
LB-PD1.2  5'-ACCGCATCGAATGCATGTCTCGGGTTACGTACCAGAATG-3' (SEQ ID NO:8)

Downstream Primers

LB-PD2.1  5'-CGATTCCGCTCCAGACTTCTCGGGTTCACAGAATATCGCC-3' (SEQ ID NO:9)
LB-PD2.2  5'-CGATTCCGCTCCAGACTTCTCGGGTTCACAGAATATCGC-3' (SEQ ID NO:.10)

Bumpers

BD1.1  5'-AAATTCTGACCAAGTT-3' (SEQ ID NO:11)
BD2.1  5'-TTTGATCTTTCTCCC-3' (SEQ ID NO:12)
Detector 1 DD1.1  5'-GGCTTTGTGGAGACA-3' (SEQ ID NO:13)
Detector 2 DD2.1  5'-GACTTTCATAATTTTGG-3' (SEQ ID NO:14)

The overall design and position of the primers, bumpers and detectors is shown in FIG. 1.

EXAMPLE 3

Optimization of Reaction Conditions for tSDA with the ltuB System

In a typical tSDA reaction, target DNA was added to tubes with the following components: glycerol, DMSO, potassium phosphate and human DNA. This mixture was boiled in a heat bath for 2–5 minutes. The sample was transferred to a 45° C. thermolock and a decontamination mix was added containing: potassium phosphate, dGTP, dCTP, dATP, primers, DTT, BSA, trehalose, magnesium acetate and UDG. The samples were incubated for 30 minutes and then transferred to a 52° C. or a 54° C. thermolock block. An amplification mixture was then added containing: potassium phosphate, dUTP, DTT, BSA, trehalose, magnesium acetate, UDI, BsoBI and Bst. The samples were again incubated for 30 minutes. All of the reactions were halted by boiling them for 5 minutes. The products of the amplification reactions were detected with an end labeled $P^{32}$ detector probe using a primer extension reaction. The detected products are separated by molecular weight on an acrylamide sequencing gel, which is both exposed using X-ray film and scanned through the use of a Molecular Dynamics phosphoimager.

A screening experiment was designed to examine the effect of different combinations of amplification primers upon product yield. This was performed using numerous tSDA buffer combinations that examined the effect of the concentration of potassium phosphate (25 mM or 35 mM), DMSO (3% or 8%), glycerol (3.5% or 7%), human DNA (650 ng or 1250 ng), and temperature (52° C. or 54° C.). All of the other components of the tSDA system were held constant. A statistically designed experiment was performed to examine various combinations of all of the mentioned variables in conjunction with primer/primer combinations. Of the conditions tested, one of the sets of conditions which yielded optimal results was:

| Amplification primers: | LB-PD1.2 (SEQ ID NO: 8) (0.5 µM) and |
| --- | --- |
| | LB-PD2.2 (SEQ ID NO: 10) (0.5 µM) |
| Bumpers: | LB-BD1.1 (SEQ ID NO: 11) (0.05 µM) and |
| | LB-BD2.1 (SEQ ID NO: 12) (0.05 µM) |
| Detector: | LB-DD1.1 (SEQ ID NO: 13) (10.0 µM) |
| Potassium phosphate, pH 7.6 | 35 mM |
| DMSO | 3% |
| Glycerol | 6–7% |
| Magnesium acetate | 5 mM |
| DTT | 0.36 mM |
| Trehalose | 1.82% |
| BSA | 100 µg/mL |
| human DNA | 650 ng |
| dCTP | 1.4 mM |
| dUTP | 0.5 mM |
| dGTP | 0.2 mM |
| dATP | 0.2 mM |
| UDG | 1 unit/50 µL reaction |
| UDI | 5 units/50 µL reaction |
| BsoBI | 160 units |
| Bst | 9 units |
| Decontamination at 45° C. for 30 minutes | |
| Amplification at 52° C. for 30 minutes | |

EXAMPLE 4

Assay of the ltuB System for Sensitivity

To test the sensitivity of the ltuB system, a series of dilutions of C. trachomatis LGV II were made from $1 \times 10^6$ genomes/5 µL down to 1 genome/5 µL. This titration of target DNA was used in a limit of detection experiment. The titration panel was tested with the ltuB tSDA system at two levels of human DNA: 650 ng and 1250 ng/reaction. The tSDA conditions used for this experiment were identical to the optimal conditions described in Example 3. Amounts of $1 \times 10^6$, $1 \times 10^5$ and $1 \times 10^4$ genomes/reaction were tested in single samples, $1 \times 10^3$ genomes/reaction was tested in duplicate, and 100, 10 and 1 genomes/reaction were tested in triplicate. A negative control was also included. The method of testing low copy numbers of the C. trachomatis genome in multiple reactions was done to ensure that the lack of amplification in one sample was not considered to be indicative of the system's sensitivity. The results of the experiment indicated an initial sensitivity down to $1 \times 10^2$ genomes/50 µL reaction.

EXAMPLE 5

Extended Assay of Crossreactivity and Specificity of the ltuB System

A crossreactivity/specificity experiment was designed for the ltuB tSDA system. Standard tSDA reactions were performed using the optimal conditions listed in Example 3. The panel of organisms tested consisted of C. trachomatis serovars and numerous crossreactants. Each of the C. trachomatis serovars was tested at $1 \times 10^4$ genomes. The crossreactant DNAs were each tested at $1 \times 10^7$ genomes. The C. trachomatis samples were tested individually but the crossreactants were examined in pools of 3–4 species per reaction. In order to determine that the lack of amplification within the crossreactant pools was due to the specificity of the ltuB system and not any inhibitors of tSDA, each pool was additionally spiked with $1 \times 10^4$ genomes of C. trachomatis (strain LGV II) and tested as controls. The results are shown in Table 2. Each of the C. trachomatis serovars was positive for amplification with the ltuB tSDA system. Also, none of the crossreactant bacterial pools had any detectable amplification occur, and each of the pools spiked with the LGV II produced the appropriate sized amplification product.

TABLE 2

| Organism | Strain | ltuB |
| --- | --- | --- |
| Chlamydia trachomatis | A | + |
| Chlamydia trachomatis | Ba | + |
| Chlamydia trachomatis | C | + |
| Chlamydia trachomatis | D | + |
| Chlamydia trachomatis | E | + |
| Chlamydia trachomatis | F | + |
| Chlamydia trachomatis | G | + |
| Chlamydia trachomatis | H | + |
| Chlamydia trachomatis | I | + |
| Chlamydia trachomatis | J | + |
| Chlamydia trachomatis | K | + |
| Chlamydia trachomatis | LGV II | + |
| Chlamydia trachomatis | LGV III | + |
| Chlamydia psittaci | | – |
| Chlamydia pneumoniae | | – |
| Neisseria gonorrhoeae | BDMS 1632 | – |
| Neisseria gonorrhoeae | ATCC 19424 | – |
| Neisseria gonorrhoeae | BDMS 2900 | – |
| Neisseria gonorrhoeae | ATCC 35541 | – |
| Neisseria meningitidis | ATCC 13090 | – |
| Neisseria meningitidis | ATCC 13077 | – |
| Neisseria lactamica | ATCC 23970 | – |
| Neisseria lactamica | ATCC 23972 | – |
| Neisseria flavescens | ATCC 13120 | – |
| Neisseria sicca | ATCC 29193 | – |
| Neisseria subflava | ATCC 14799 | – |
| Neisseria cinerea | ATCC 14685 | – |
| Neisseria elongata | ATCC 25295 | – |
| Neisseria mucosa | ATCC 19696 | – |
| Branhamella catarrhalis | ATCC 25240 | – |
| Moraxella lacunata | ATCC 17967 | – |
| Kingella kingae | ATCC 23330 | – |
| Salmonella typhimurium | ATCC 13311 | – |
| Salmonella minnesota | ATCC 9700 | – |
| Staphylococcus aureus | ATCC 12598 | – |
| Acinetobacter lwoffi | ATCC 19001 | – |
| E. coli | ATCC 11775 | – |
| Klebsiella pneumoniae | ATCC 13883 | – |
| Gardnerella vaginalis | ATCC 14018 | – |
| Streptococcus Group A | ATCC 16915 | – |
| Streptococcus Group B | ATCC 12386 | – |
| Proteus mirabilis | ATCC 29906 | – |
| Haemophilus influenzae B | ATCC 33533 | – |
| Mycoplasma orale | ATCC 23714 | – |
| HSV-1 | McINTYRE | – |
| HSV-2 | Strain G | – |
| Trichomonas vaginalis | ATCC 30001 | – |
| Candida albicans | ATCC 44808 | – |
| Streptococcus faecalis | ATCC 29212 | – |
| Peptostreptococcus productus | ATCC 27340 | – |

While the invention has been described with some specificity, modifications apparent to those with ordinary skill in the art may be made without departing from the scope of the invention. Various features of the invention are set forth in the following claims.

What is claimed is:

1. A nucleic acid selected from the group consisting of LB-PD1.1 (SEQ ID NO:7) and LB-PD1.2 (SEQ ID NO:8).

2. A nucleic acid selected from the group consisting of LB-PD2.1 (SEQ ID NO:9) and LB-PD2.2 (SEQ ID NO:10).

3. A nucleic acid selected from the group consisting of BD 1.1 (SEQ ID NO:11) and BD2.1 (SEQ ID NO:12).

4. A nucleic acid selected from the group consisting of DD1.1 (SEQ ID NO:13), a nucleic acid complementary to SEQ ID NO:13, DD2.1 (SEQ ID NO:14) and a nucleic acid complementary to SEQ ID NO:14.

5. The nucleic acid of claim 4 wherein said nucleic acid comprises a detectable marker.

6. The nucleic acid of claim 5 wherein said detectable marker is selected from the group consisting of a radioactive marker and a fluorescence marker.

7. A nucleic acid selected from the group consisting of ltuB-1 (SEQ ID NO:1), ltuB-2 (SEQ ID NO:2), ltuB-3 (SEQ ID NO:3), ltuB-4 (SEQ ID NO:4), ltuB-5 (SEQ ID NO:5) and ltuB-6 (SEQ ID NO:6).

8. A kit comprising:
a) one or more primers selected from the group consisting of LB-PD1.1 (SEQ ID NO:7) and LB-PD1.2 (SEQ ID NO:8),
b) one or more primers selected from the group consisting of LB-PD2.1 (SEQ ID NO:9) and LB-PD2.2 (SEQ ID NO:10),
c) bumpers BD1.1 (SEQ ID NO:11) and BD2.1 (SEQ ID NO:12), and
d) one or more detectors selected from the group consisting of DD1.1 (SEQ ID NO:13), a nucleic acid complementary to SEQ ID NO:13, DD2.1 (SEQ ID NO:14) and a nucleic acid complementary to SEQ ID NO:14.

9. The kit of claim 8 wherein said detector comprises a detectable marker.

10. A method for detecting the presence or absence of Chlamydia trachomatis in a sample, said method comprising the steps of:
a) treating said sample using a pair of nucleic acid primers in a nucleic acid amplification reaction wherein a first primer is selected from the group consisting of LB-PD1.1 (SEQ ID NO:7) and LB-PD1.2 (SEQ ID NO:8) and a second primer is selected from the group consisting of LB-PD2.1 (SEQ ID NO:9) and LB-PD2.2 (SEQ ID NO:10), and
b) detecting any amplified nucleic acid product, wherein detection of amplified product indicates the presence of Chlamydia trachomatis.

11. The method of claim 10 wherein said nucleic acid amplification reaction is a Strand Displacement Amplification (SDA) reaction.

12. The method of claim 11 wherein said SDA reaction utilizes BD 1.1 (SEQ ID NO:11) and BD2.1 (SEQ ID NO:12) as bumpers.

13. The method of claim 10 wherein detecting said amplified nucleic acid product is conducted by hybridizing said amplified nucleic acid product with a detector selected from the group consisting of DD1.1 (SEQ ID NO:13), a nucleic acid complementary to SEQ ID NO:13, DD2.1 (SEQ ID NO:14) and a nucleic acid complementary to SEQ ID NO:14.

14. The method of claim 11 wherein said SDA reaction is a thermophilic Strand Displacement Amplification (tSDA) reaction.

15. The method of claim 14 wherein said tSDA reaction is a homogeneous fluorescent real time tSDA reaction.

16. The method of claim 14 wherein said tSDA reaction utilizes BD1.1 (SEQ ID NO:11) and BD2.1 (SEQ ID NO:12) as bumpers.

17. The method of claim 14 wherein detecting said amplified nucleic acid product is conducted by hybridizing said amplified nucleic acid product with a detector selected from the group consisting of DD1.1 (SEQ ID NO:13), a nucleic acid complementary to SEQ ID NO:13, DD2.1 (SEQ ID NO:14) and a nucleic acid complementary to SEQ ID NO:14.

18. The method of claim 16 wherein said first primer is LB-PD1.2 (SEQ ID NO:8) and said second primer is LB-PD2.2 (SEQ ID NO:10).

19. The method of claim 18 wherein detecting said amplified nucleic acid product is conducted by hybridizing said amplified nucleic acid product with detector DD1.1 (SEQ ID NO:13) or a nucleic acid complementary to SEQ ID NO:13.

* * * * *